(12) United States Patent
Hsieh et al.

(10) Patent No.: US 11,951,233 B2
(45) Date of Patent: Apr. 9, 2024

(54) ACELLULAR ORGANS, AND METHODS OF PRODUCING THE SAME

(71) Applicant: ACRO BIOMEDICAL COMPANY. LTD., Kaohsiung (TW)

(72) Inventors: Dar-Jen Hsieh, Kaohsiung (TW); Chao-Yi Wei, Kaohsiung (TW); Chao-Chin Chao, Kaohsiung (TW); Jer-Cheng Kuo, Kaohsiung (TW); Yi-Ping Lai, Kaohsiung (TW); Srinivasan Periasamy, Kaohsiung (TW)

(73) Assignee: ACRO BIOMEDICAL COMPANY. LTD., Kaohsiung (TW)

( * ) Notice: Subject to any disclaimer, the term of this patent is extended or adjusted under 35 U.S.C. 154(b) by 712 days.

(21) Appl. No.: 17/251,790

(22) PCT Filed: Sep. 11, 2019

(86) PCT No.: PCT/CN2019/105300
§ 371 (c)(1),
(2) Date: Dec. 12, 2020

(87) PCT Pub. No.: WO2020/052580
PCT Pub. Date: Mar. 19, 2020

(65) Prior Publication Data
US 2021/0205497 A1 Jul. 8, 2021

Related U.S. Application Data

(60) Provisional application No. 62/729,983, filed on Sep. 11, 2018.

(51) Int. Cl.
*A61K 36/00* (2006.01)
*A61L 27/36* (2006.01)

(52) U.S. Cl.
CPC ....... *A61L 27/3691* (2013.01); *A61L 27/3625* (2013.01); *A61L 27/3687* (2013.01); *A61L 2430/20* (2013.01); *A61L 2430/40* (2013.01)

(58) Field of Classification Search
CPC .............................. A61L 2430/40; Y02P 20/54
See application file for complete search history.

(56) References Cited

PUBLICATIONS

Seo, Decellularized heart ECM hydrogel using supercritical carbon dioxide for improved angiogenesis. Acta biomaterialia, (20180200) vol. 67, pp. 270-281 (Year: 2018).*

\* cited by examiner

*Primary Examiner* — Qiuwen Mi
(74) *Attorney, Agent, or Firm* — NZ CARR LAW OFFICE

(57) ABSTRACT

Provided are methods of producing an acellular organ. The method includes the steps of, subjecting an organ derived from an animal to a static supercritical fluid (SCF) treatment followed by a dynamic SCF treatment. Optionally, the method of the present disclosure further includes a hypertonic and a hypotonic treatments prior to the static SCF treatment, and/or a neutralizing treatment after the dynamic SCF treatment. Also disclosed herein are acellular organs produced by the present method.

18 Claims, 19 Drawing Sheets

| Rabbit | Before treatment | After treatment |
|---|---|---|
| Ventricle |  |  |
| Atrium |  |  |
| Aorta |  |  |

| Chicken | Before treatment | After treatment |
|---|---|---|
| Outer surface |  |  |
| Inner surface |  |  |
| Inner surface of Apex |  |  |

| Rabbit | Before treatment | After treatment |
|---|---|---|
| Atrium |  |  |
| Ventricle |  |  |

ACELLULAR ORGANS, AND METHODS OF PRODUCING THE SAME

CROSS REFERENCE TO RELATED APPLICATION

This application is a U.S. National Stage Filing under 35 U.S.C. 371 from International Patent Application Serial No. PCT/CN2019/105300, filed Sep. 11, 2019, and published on Mar. 19, 2020, which claims the priority of U.S. Ser. No. 62/729,983, filed Sep. 11, 2018, the disclosure of which are incorporated by reference herein in their entireties.

BACKGROUND OF THE INVENTION

1. Field of the Invention

The present disclosure in general relates to the field of producing acellular organs. More particularly, the present disclosure relates to improved methods of producing acellular organs suitable as xenografts for the treatment of various diseases, for example, heart diseases.

2. Description of Related Art

Heart diseases refer to various types of conditions that affect heart function. Common heart diseases include coronary heart disease (CHD), valvular heart disease, cardiomyopathy, arrhythmias, and inflammatory heart disease. According to the reports of World Health Organization (WHO), more than 17 million people die annually from cardiovascular disease. The classic signs and symptoms associated with heart diseases include, chest pain, breathlessness, sweating, nausea, irregular heartbeat, weakness, and dizziness. Risk factors for the development of heart diseases include, smoking, hypertension, high cholesterol, diabetes, obesity, alcohol, poor diet, and physical inactivity.

Heart transplantation is a surgical transplant procedure performed on patients with end-stage heart failure or severe heart diseases when other medical or surgical treatments have failed. Approximately 3,500 heart transplantations are performed every year in the world, more than half of which occur in the United States. In addition to infection and sepsis, organ rejection is one of the most serious complications of heart transplantation. Specifically, the transplanted heart originating from another organism generally induces a rejection response in the recipient. For the purposes of suppressing or lessening such a rejection response, the patients have to be administered with immunosuppressive drugs for the rest of their life. However, the administration of immunosuppressive drugs may cause unwanted side effects, such as increased likelihood of infection and/or development of cancers.

In view of the foregoing, there exists in the related art a need for an improved method for producing a heart, in which the native structure and conformation of a native heart are preserved, while immunogenic matters (e.g., cells and/or enzymes) are reduced to a level that the thus-produced heart may serve as a three-dimensional scaffold for host cells to grow thereon after transplantation without eliciting undesired rejection responses.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

The first aspect of this disclosure is directed to a method for producing an acellular organ (e.g., an acellular heart), which is characterized by the preservation of its native structure and conformations while eliminating immunogenicity residues (e.g., cellular matters). The thus-produced acellular organ is suitable for use in tissue transplantation. The method for producing an acellular organ comprises the steps of, (a) subjecting an organ to a first supercritical fluid (SCF) in the presence of a first co-solvent under a first pressure of 200-500 bar at a first temperature between 30-50° C. for a first period of 10-100 minutes; and (b) subjecting the first SCF treated organ of the step (a) with a continuous flow of a second SCF in the presence of a second co-solvent under a second pressure of 200-500 bar at a second temperature between 30-50° C. for a second period of 10-100 minutes, wherein the flow rate of the second SCF is 10-30 liter per minute.

According to embodiments of the present disclosure, the present method does not comprise the step of treating the organ with an agent selected from the group consisting of an enzyme, an ion chelating agent, a detergent, a glycerol, and a combination thereof.

According to certain embodiments of the present disclosure, the first and second SCFs are independently selected from the group consisting of supercritical carbon dioxide ($ScCO_2$), supercritical nitrous oxide ($ScN_2O$), supercritical alkane, supercritical alkene, supercritical alcohol, supercritical acetone, and a combination thereof. In some working examples, each of the first and second SCFs is $ScCO_2$.

According to some embodiments, in the step (a), the organ is subjected to $ScCO_2$ under a pressure of 350 bar at 40° C. for a first period of 10-80 minutes; and then in the step (b), the product of step (a) is subjected to a continuous flow of $ScCO_2$ at a flow rate of 20 liter per minute under a pressure of 350 bar at 40° C. for a second period of 10-80 minutes. In one embodiment, the first period is 30 minutes, and the second period is 60 minutes. In another embodiment, the first period is 10 minutes, and the second period is 80 minutes. In still another embodiment, the first period is 80 minutes, and the second period is 10 minutes.

Each of the first and second co-solvents preferably is 30-100% (vol %) ethanol. According to some specific examples, each of the first and second co-solvents is 75% (vol %) ethanol.

Optionally, prior to the step (a), the present method further comprises, (1) immersing the organ in a hypertonic solution for 10-60 minutes; and (2) immersing the hypertonic solution treated organ of the step (1) in a hypotonic solution for 10-60 minutes.

According to certain embodiments of the present disclosure, the hypertonic solution is a salt solution containing 0.5-4.0 M NaCl, and the hypotonic solution is water. According to some working examples, the organ is immersed in the salt solution containing 2.0 M NaCl for 30 minutes (step (1)), and then immersed in the water for 30 minutes (step (2)). In certain preferred examples, the steps (1) and (2) are repeated for at least two times.

Still optionally, after the step (b), the present method further comprises the step of subjecting the second SCF treated organ to a solution containing 0.01-1.0 N NaOH.

Preferably, the second SCF treated organ is subjected to a solution containing 0.1 N NaOH.

Examples of organ suitable to be treated by the present method include, but are not limited to, a heart, an intestine, a lung, a spleen, a kidney, a liver, a stomach, a pancreas, a bladder, a colon, a rectum, or a brain. According to certain embodiments of the present disclosure, the organ is a heart.

The organ treated by the present method may be isolated or derived from an animal, for example, a pig, a cow, a sheep, a goat, a rabbit, a monkey, a chicken, or a human.

Also disclosed herein is an acellular organ (e.g., an acellular heart) produced by the present method in accordance with any embodiments of the present disclosure.

As mentioned above, the present acellular organ is mainly constituted by collagens, in which their native structures and conformations are preserved, so that they may serve as a three-dimensional bio-scaffold that allows cells to grow thereon and/or therein after being applied to a subject (e.g., transplantation). Further, the thus-produced organ is acellular, meaning it is devoid of any cellular matter; such an acellular organ is substantially non-immunogenic and will not induce any immunogenic response in the transplanted subject.

It is therefore another aspect of the present disclosure to provide a method of treating a disease in a subject by the use of the present acellular organ or a portion thereof. The method comprises transplanting the present acellular organ or a portion thereof to the subject so as ameliorate or alleviate the symptoms associated with the disease. According to some embodiments, the subject suffers from a heart disease, and an acellular heart produced by the present method is transplanted to the subject thereby improving the cardiac function of the subject, and/or ameliorate or alleviate the symptoms associated with the heart disease. Optionally, the acellular heart for the treatment of heart diseases has cells cultivated thereon/therein; for example, having cardiomyocytes, pacemaker cells, stem cells, or a combination thereof cultivated thereon/therein. Depending on intended purposes, the cells cultivated may be autologous or allogenic.

The heart disease treatable with the present method may be any of coronary heart disease, valvular heart disease, myocardial infarction, congestive heart failure, myocardial damage, myocardial ischemia, inflammatory heart disease (e.g., endocarditis, inflammatory cardiomegaly, or myocarditis), cardiomyopathy, arrhythmias, or myocardial fibrosis.

Many of the attendant features and advantages of the present disclosure will becomes better understood with reference to the following detailed description considered in connection with the accompanying drawings.

BRIEF DESCRIPTION OF THE DRAWINGS

The present description will be better understood from the following detailed description read in light of the accompanying drawings, where:

FIGS. 2A and 2B: the photographs (at the magnitude of 400×) of hearts before and after S30-D60 decellularizing procedure, in which the hearts were isolated from rabbits (FIG. 2A) or chicken (FIG. 3B). FIGS. 2C and 2D: the photographs of S10-D80 and S80-D10 acellular hearts at the magnitude of 40× or 100×.

FIG. 3A: the photographs (at the magnitude of 100×) of hearts before and after S30-D60 decellularizing procedure. FIGS. 3B and 3C: the photographs of S10-D80 and S80-D10 acellular hearts at the magnitude of 40× or 100×.

FIG. 7A: the morphology of hearts before and after the SCF treatment. FIG. 7B: the photographs of H&E staining at the magnitude of 40× or 100× that depict residual cells remaining in the decellularizing hearts after the treatment. FIG. 7C: the photographs of DAPI staining at the magnitude of 40× or 100× that depict the level of DNA molecules in the decellularizing hearts. The residual cells and DNA molecules were respectively indicated by arrows in FIGS. 7B and 7C.

FIG. 8A: the morphology of hearts before and after the detergent treatment. FIG. 8B: the photographs of H&E staining at the magnitude of 40× or 100× that depict residual cells remaining in the decellularizing hearts after the treatment. FIG. 8C: the photographs of DAPI staining at the magnitude of 40× or 100× that depict the level of DNA molecules in the decellularizing hearts. The residual cells and DNA molecules were respectively indicated by arrows in FIGS. 8B and 8C.

FIG. 9A: the morphology of hearts before and after the static SCF treatment. FIG. 9B: the photographs of H&E staining at the magnitude of 40× or 100× that depict residual cells remaining in the decellularizing hearts after the treatment. FIG. 9C: the photographs of DAPI staining at the magnitude of 40× or 100× that depict the level of DNA molecules in the decellularizing hearts. Neither residual cells nor DNA molecules were detected in FIGS. 9B and 9C.

DETAILED DESCRIPTION OF THE INVENTION

Figure 1A:
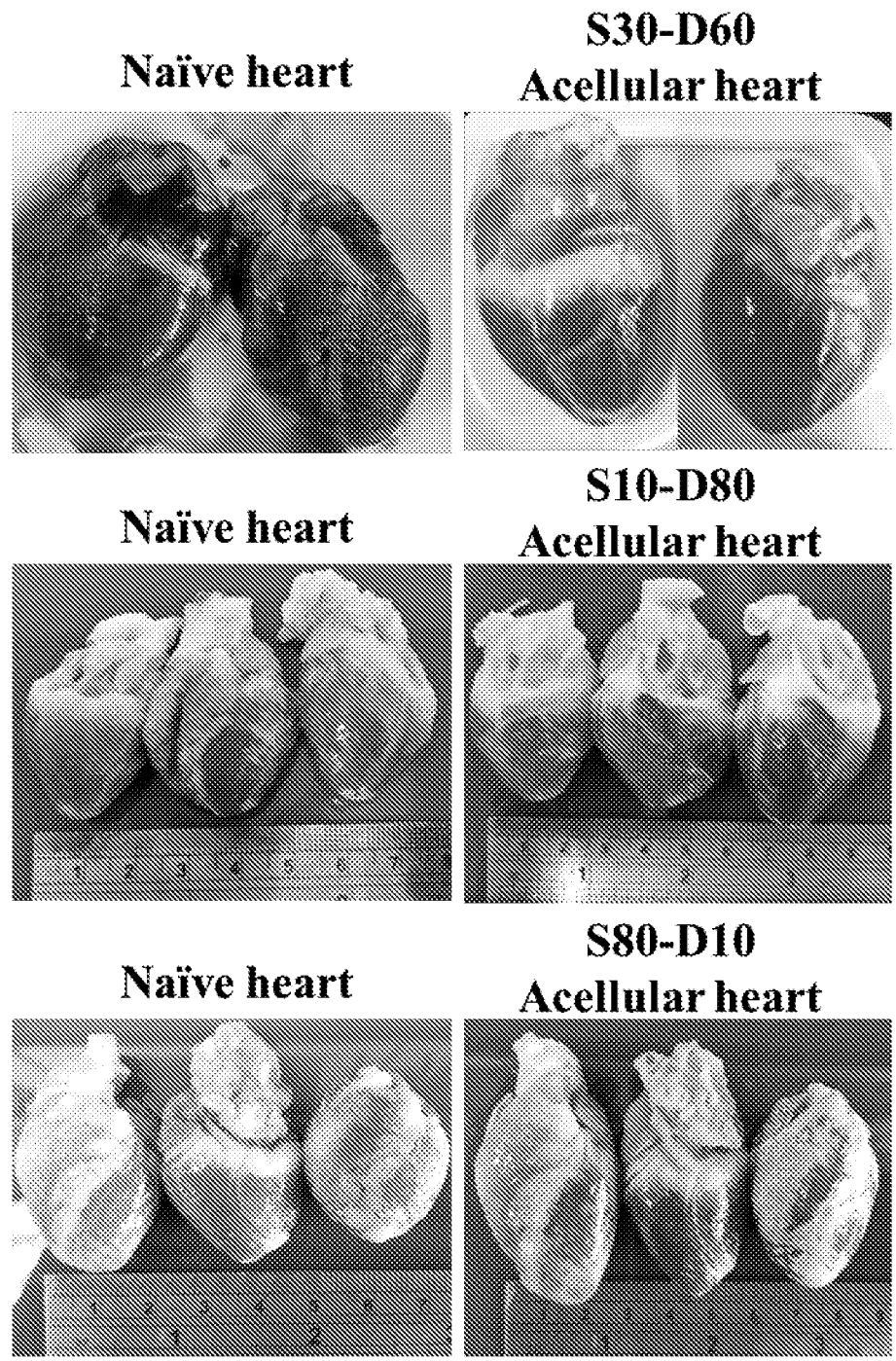
FIG. 1A are photographs of hearts before (left photographs) and after (right photographs) specified decellularizing procedures according to Example 1.2 of the present disclosure, wherein the hearts were isolated from rabbits.

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

I. Definition

For convenience, certain terms employed in the specification, examples and appended claims are collected here. Unless otherwise defined herein, scientific and technical terminologies employed in the present disclosure shall have the meanings that are commonly understood and used by one of ordinary skill in the art. Also, unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Also, as used herein and in the claims, the terms "at least one" and "one or more" have the same meaning and include one, two, three, or more.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about". Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

The term "hypertonic solution" as used herein refers to a solution having a higher concentration of a solute (e.g., NaCl) than that in the organ (e.g., heart) that comes into contact with or immersed in the solution, so that water molecules are drawn out from the organ and into the solution by osmosis. In contrast, the term "hypotonic solution" refers to a solution having a lower concentration of a solute (e.g., NaCl) than that in the organ (e.g., heart) that comes into contact with or immersed in the solution, so that water molecules are drawn from the solution and into the organ by osmosis.

The term "subject" refers to a mammal including the human species that is treatable with acellular organs (e.g., acellular hearts) and/or methods of the present invention. The term "subject" is intended to refer to both the male and female gender unless one gender is specifically indicated.

II. Description of the Invention

The present disclosure aims at providing an improved method of producing an acellular organ (such as, an acellular heart), the acellular organ produced therefrom, and uses of the thus-produced acellular organ in the treatment of various diseases (e.g., heart diseases).

The first aspect of the present disclosure is thus directed to a method of producing an acellular organ, in which the native structure and conformation of the acellular organ is preserved. Based on the characteristics of low immunogenicity, the thus-produced acellular organ may serve as an optimal bio-scaffold for supporting cell growth thereon/therein without inducing any undesired rejection response in the transplanted patients.

The method for producing an acellular organ comprises,
(a) subjecting an organ to a first SCF in the presence of a first co-solvent under a first pressure of 200-500 bar at a first temperature between 30-50° C. for a first period of 10-100 minutes; and
(b) subjecting the first SCF treated organ of the step (a) with a continuous flow of a second SCF in the presence of a second co-solvent under a second pressure of 200-500 bar at a second temperature between 30-50° C. for a second period of 10-100 minutes, wherein the flow rate of the second SCF is 10-30 liter per minute.

The present method is characterized in not comprising the step of treating the organ with any of the agents selecting from the group consisting of an enzyme, an ion chelating agent, a detergent, a glycerol, and a combination thereof.

Before starting the present method, the organ is first harvested from an animal. Animals suitable for use in the present disclosure include, but are not limited to, pig, cow, sheep, goat, rabbit, monkey, chicken, and human. Depending on desired purposes, the organ treated by the present method may be a heart, intestine, lung, spleen, kidney, liver, stomach, pancreas, bladder, colon, rectum, or brain. According to certain embodiments of the present disclosure, the organ is a heart harvested from a chicken. According to alternative embodiments, the organ is a heart harvested from a rabbit. Preferably, the organ is a heart harvested from a human or a pig.

The harvested organ (e.g., heart) is then subjected to a static treatment of SCF as described in the step (a). Specifically, the organ is statically immersed in SCF in the presence of a first co-solvent under a first pressure of 200-500 bar at a first temperature between 30-50° C. for a first period of about 10-100 minutes. Examples of the SCF suitable for statically treating the organ include, but are not limited to, $ScCO_2$, $ScN_2O$, supercritical alkane, supercritical alkene, supercritical alcohol, supercritical acetone, and a combination thereof. In one example, the SCF is $ScCO_2$.

The first co-solvent is a $C_{1-4}$ alcohol, which may be selected from the group consisting of ethanol, propanol, isopropanol, butanol, isobutanol, sec-butanol, t-butanol, and cyclobutanol. According to some embodiments, the first co-solvent is 30-100% (vol %) ethanol, such as 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 (vol %) ethanol. Preferably, the first co-solvent is 50-90% (vol %) ethanol. More preferably, the first co-solvent is 70-80% (vol %) ethanol, such as 70, 75 or 80% (vol %) ethanol. In one specific example, the first co-solvent is 75% (vol %) ethanol.

The static treatment is performed at a condition, in which the pressure is about 200-500 bar, such as 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 bar; and the temperature is between 30-50° C., such as 30, 31, 32, 33, 34, 35, 36, 37, 38, 39, 40, 41, 42, 43, 44, 45, 46, 47, 48, 49 or 50° C. Preferably, the pressure is about 300-400 bar, and the temperature is about 35-45° C. The period for the static treatment is about 10-100 minutes, for example, 10, 15, 20, 25, 30, 35, 40, 45, 50, 55, 60, 65, 70, 75, 80, 85, 90, 95, or 100 minutes; preferably, the treatment period is about 10-80 minutes.

After the static treatment, the organ is further subjected to a dynamic treatment of SCF as described in the step (b). In this step, the SCF is pumped through the product of step (a) at a flow rate of about 0.1-100 liter per minute; for example, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 liter per minute. Preferably, the flow rate of the SCF is about 1-50 liter per minute. More preferably, the flow rate of the SCF is about 10-30 liter per minute. In one working example of the present disclosure, the flow rate is about 20 liter per minute.

The SCF of step (b) may be any of $ScCO_2$, $ScN_2O$, supercritical alkane, supercritical alkene, supercritical alcohol, supercritical acetone, or a combination thereof. As could be appreciated, the SCFs of steps (a) and (b) may be the same or different. According to one specific example, both SCFs of steps (a) and (b) are $ScCO_2$.

The second co-solvent of step (b) is a $C_{1-4}$ alcohol, for example, ethanol, propanol, isopropanol, butanol, isobutanol, sec-butanol, t-butanol, or cyclobutanol. According to certain embodiments, the second co-solvent is 30-100% (vol %) ethanol, such as 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 (vol %) ethanol. Preferably, the second co-solvent is 50-90% (vol %) ethanol. More preferably, the second co-solvent is 70-80% (vol %) ethanol, such as 70, 75 or 80% (vol %) ethanol. In one specific example, the second co-solvent is 75% (vol %) ethanol. It would be appreciated that the co-solvents of steps (a) and (b), i.e., the first and the second co-solvents, may be the same or different. A skilled artisan may independently select suitable agents (e.g., $C_{1-4}$ alcohol) as the first and second co-solvents, and adjust their concentration in accordance with the practical uses.

The dynamic treatment is performed under a pressure of about 200-500 bar at a temperature of about 30-50° C.; that is, the pressure for the dynamic treatment may be set to 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 bar; and the temperature may be set to 30, 31, 32, 33, 34, 35, 36, 37, 38, 39, 40, 41, 42, 43, 44, 45, 46, 47, 48, 49 or 50° C. Preferably, the pressure is set to about 300-400 bar, and the temperature is set to about 35-45° C. The period for the dynamic treatment is about 10-100 minutes, such as 10, 15, 20, 25, 30, 35, 40, 45, 50, 55, 60, 65, 70, 75, 80, 85, 90, 95, or 100 minutes; preferably, the treatment period is about 10-80 minutes.

As could be appreciated, the specific periods for the static and dynamic treatments may vary with factors such as the type of SCF selected, the treatment pressure and temperature, and the flow rate of the dynamic treatment. According to one embodiment, the organ is subjected to the static $ScCO_2$ treatment under the pressure of 350 bar at 40° C. for 30 minutes, and then subjected to the dynamic $ScCO_2$ treatment at a flow rate of 20 liter per minute under the pressure of 350 bar at 40° C. for 60 minutes. According to another embodiment, the organ is subjected to the static $ScCO_2$ treatment under the pressure of 350 bar at 40° C. for 10 minutes, and then subjected to the dynamic $ScCO_2$ treatment at a flow rate of 20 liter per minute under the pressure of 350 bar at 40° C. for 80 minutes. According to still another embodiment, the organ is subjected to the static $ScCO_2$ treatment under the pressure of 350 bar at 40° C. for 80 minutes, and then subjected to the dynamic $ScCO_2$ treatment at a flow rate of 20 liter per minute under the pressure of 350 bar at 40° C. for 10 minutes.

Depending on practical situations (e.g., the type or size of the decellularized organ), a skilled artisan may adjust one or more afore-mentioned operational parameters of the static and dynamic treatments, including the type of SCFs and co-solvents, the concentration of co-solvents, the treatment period, pressure and temperature, and the flow rate of the dynamic treatment, so as optimize the decellularizing procedure.

Optionally, prior to the step (a), the present method further comprises the step of subjecting the organ to a hypertonic and a hypotonic treatments thereby destroying cellular structures. According to certain embodiments of the present disclosure, the hypertonic treatment comprises immersing the organ in a salt solution containing 0.5-4.0 M (e.g., 0.5, 0.6, 0.7, 0.8, 0.9, 1, 1.5, 2, 2.5, 3, 3.5, or 4 M) NaCl for 10-60 minutes, and the hypotonic treatment comprises immersing the organ in water for 10-60 minutes. According to some working examples of the present disclosure, the organ is soaked in a salt solution containing 2.0 M NaCl for 30 minutes followed by the treatment of water for another 30 minutes. Preferably, the hypertonic and hypotonic treatments are repeated for at least two times, i.e., the organ is subjected to the hypertonic and hypotonic treatments for at least three times.

Still optionally, after the step (b), the present method further comprises the step of subjecting the product of step (b) (i.e., the dynamic SCF treated organ) to a solution containing NaOH for neutralizing the pH value of the acellular organ and removing any contaminated pathogen (e.g., bacteria or viruses) in and/or on the acellular organ. According to certain embodiments of the present disclosure, the solution contains 0.01-1.0 N NaOH; for example, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, or 1.0 N NaCl. In one working example, the product of step (b) is soaked in 0.1 N NaOH for a period of time until the pH value reaches 7.0.

Preferably, after each steps, the organ is washed with copious amounts of water to remove any soluble matters, before being subjected to the next treatment.

The present method is characterized in not having the steps of subjecting the organ to an enzymatic digestion (e.g., protease, nuclease, or glycosidase treatment), and/or an ion chelation treatment (e.g., by use of an ion chelating agent). Nor has the organ of the present invention been subjected to the treatment of a detergent. The enzymatic digestion herein refers to treating the organ with a protease, example of which includes, but is not limited to, pepsin, trypsin, chymotrypsin, papain, chymopapain, bromelain, actinidain, proteinase A, proteinase K, peptidase, ficin, calpain, caspase, and a combination thereof; a nuclease, which may be a DNA nuclease or a RNA nuclease; or a glycosidase, which may be any of cellulose, amylase, lactase, chitinase, sucrose, maltase, neuraminidase, invertase, hyaluronidase or lysozyme. The ion chelation treatment herein refers to treating the organ with a metal ion chelating agent, example of which includes, but is not limited to, ethylenediamine tetraacetic acid (EDTA), 1,4,7,10-tetraazacyclododecane-1, 4,7,10-tetraacetic acid (DOTA), 1,4,7,10-tetraazacyclododecane-1,4,7,1-0-tetrakis(methylene phosphonic acid) (DOTP), trans-1,2-diaminocyclohexant-etra-acetic acid (CDTA), 4,5-dihydroxybenzene-1,3-disulphonic acid (Tiron), thiourea, 8-hydroxyquinoline-5-sulphonic acid, 3,6-disulpho-1,8-dihydroxy-naphthalene, Eriochromeschwarz T (1-(1-hydroxy-2-naphthylazo)-2-hydroxy-5-nitro-4-naphthalene sulphonic acid), and ammonium purpurate. The detergent treatment herein refers to treating the organ with a detergent, particularly a liquid detergent consists of amphiphilic molecules, such as surfactants that are cationic (e.g., quaternary ammonium compounds), anionic (e.g., alkylbenzesulfonates, bile acids and the like) or non-ionic (e.g., Tween, Triton and/or Brij series). Further, nor does the organ of the present invention need to be immersed in a glycerol solution either, as required by some conventional processes.

Another aspect of the present disclosure is directed to an acellular organ (e.g., an acellular heart) produced by the method in accordance with any embodiment mentioned above. The thus-produced acellular organ retains the integrity of collagen fibers of a native organ, and is devoid of any cellular matter that may elicit an immune response in the patent receipted the transplanted organ. According to some examples of the present disclosure, the acellular organ produced by the present method appears to be semi-transparent, while maintains the native conformation of blood vessels.

The present disclosure also provides a method of treating a subject having a disease (e.g., a heart disease) by use of an acellular organ (e.g., an acellular heart) produced by the above-mentioned method. The method for treating a disease comprises transplanting the present acellular organ (e.g., the acellular heart) or a portion thereof to the subject.

The acellular organ produced by the method described above is suitable for use as a bio-scaffold for cells to grow therein and/or thereon, accordingly, in some optional embodiments, the acellular organ of the present disclosure may be pre-cultivated with cells in vitro before the transplantation. The cells may be cultivated in accordance with any cell cultivating technique known in the art. The cells cultivated in and/or on the acellular organ of the present disclosure may be cardiomyocytes, pacemaker cells, stem cells, or a combination thereof. Depending on intended uses, the cells may be autologous (i.e., derived from the host receiving the acellular organ as a graft) or allogenic (i.e., derived from a subject that is other than the host).

Exemplary diseases treatable with the present acellular organ and/or method include, but are not limited to, a heart, intestine, lung, spleen, kidney, liver, stomach, pancreas, bladder, colon, rectum, and brain diseases. Non-limiting examples of the heart disease treatable by the present acellular organ and/or method include a coronary heart disease, valvular heart disease, myocardial infarction, congestive heart failure, myocardial damage, myocardial ischemia, inflammatory heart disease (for example, endocarditis, inflammatory cardiomegaly, or myocarditis), cardiomyopathy, arrhythmias, and myocardial fibrosis.

The subject treatable with the present acellular organ and/or method may be a pig, a cow, a sheep, a goat, a rabbit, a monkey, a chicken, or a human. Preferably, the subject is a human.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety.

EXAMPLE

Materials and Methods

Hematoxylin and Eosin Staining (H&E Staining)

The heart section was de-paraffinized by immersing in xylene for 10 minutes, and the treatment was repeated once. The de-paraffinized tissue was then hydrated by passing through a series of alcohol bath, in which the alcohol concentration varied from 100%, to 95%, 85%, and 75%, respectively. In each pass, the tissue sample was allowed to stay in the alcohol solutions for 2 minutes, then rinsed with copious amount of deionized water. After hydration, the tissue sample was stained with hematoxylin for 3-5 minutes, then washed with de-ionized water and 75% ethanol. The hematoxylin stained cartilage was further stained with 1% Eosin Y for about 30 seconds, followed by washing with deionized water, and 95% and 100% ethanol, sequentially.

DAPI Staining

The heart section was equilibrated with phosphate-buffered saline (PBS), followed by adding the DAPI staining solution (300 nM) and incubated at room temperature for 1-5 minutes. The sample was washed by PBS for 3-5 times. The DAPI-staining cells were detected by a fluorescence microscope with appropriate filters.

Example 1 Acellular Heart Produced by Static and Dynamic SCF Treatments

Three decellularizing procedures for removing cellular matters, such as, whole cells, cellular debris, and cellular component (e.g., protein, nucleic acid, and lipid) from target tissues or organs (for example, heart), were exemplified in this example. All three decellularizing procedures exemplified in this example comprises a hypertonic and a hypotonic treatments followed by a static and a dynamic SCF treatments under specified conditions, and then a neutralization step. The details of the decellularizing procedures were described in Example 1.1, and the thus-produced acellular products were characterized in Example 1.2.

1.1 Preparation of Acellular Heart (1) Hypertonic and Hypotonic Treatments

The heart harvested from rabbits or chickens was first immersed in water for about 24 hours followed by a hypertonic and a hypotonic treatments (i.e., being soaked in NaCl solution (2 M) at room temperature for 30 minutes, and then in water at room temperature for another 30 minutes) for three times. The hypertonic/hypotonic treated heart was then washed with copious amounts of water to remove any residual salt.

(2) Static and Dynamic SCF Treatments

Next, the heart was placed on a tissue holder, which was then inserted into a vessel of a $ScCO_2$ system (HELIX™, Super Critical Fluid Extractor (SFE) system), in which 100 ml ethanol (75%) was present in the vessel. The $ScCO_2$ system was then operated at a pressure of 350 bar, at 40° C. for a static $ScCO_2$ treatment for 10, 30, or 80 minutes followed by a dynamic $ScCO_2$ treatment with a flow rate of about 20 liter per minute for 80, 60, or 10 minutes, so as to remove any residual cellular matters, and thereby generating the decellularized heart.

(3) Neutralization

Each decellularized heart was then treated with 0.1 N NaOH until the pH value reached 7.0, and washed with water for 10 minutes. All the acellular hearts were stored at a sterilized condition until use.

The thus-produced acellular hearts were respectively designated as S30-D60, S10-D80, and S80-D10 acellular hearts in accordance with their SCF treatment conditions. Specifically, (1) S30-D60 acellular heart referred to the heart produced by the S30-D60 decellularizing procedure, which comprised the hypertonic/hypotonic treatment followed by the static $ScCO_2$ treatment for 30 minutes, and the dynamic $ScCO_2$ treatment for 60 minutes, and then the neutralization step;

(2) S10-D80 acellular heart referred to the heart produced by the S10-D80 decellularizing procedure, which comprised the hypertonic/hypotonic treatment followed by the static $ScCO_2$ treatment for 10 minutes, and the dynamic $ScCO_2$ treatment for 80 minutes, and then the neutralization step; and (3) S80-D10 acellular heart referred to the hearts produced by the S80-D10 decellularizing procedure, which comprised the hypertonic/hypotonic treatment followed by the static $ScCO_2$ treatment for 80 minutes, and the dynamic $ScCO_2$ treatment for 10 minutes, and then the neutralization step.

1.2 Characterization of Acellular Heart

Figure 1B:
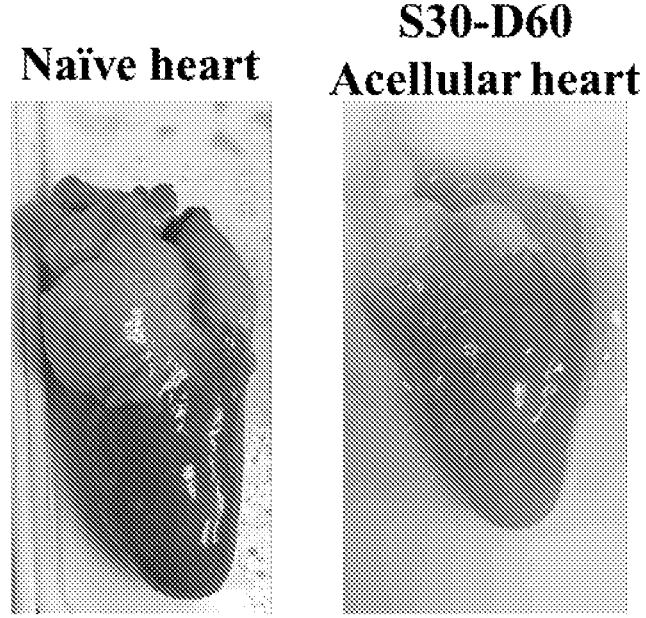
FIG. 1B are photographs of hearts before (left photograph) and after (right photograph) specified decellularizing procedures according to Example 1.2 of the present disclosure, wherein the hearts were isolated from chickens.

The morphology of the acellular hearts produced in Example 1.1 was examined under microscope, and the results were respectively depicted in FIGS. 1A and 1B. The photographs of FIG. 1A were directed to the rabbit hearts before and after the decellularizing treatment; the data indicated that none of the treatments affected the structure of hearts. Similar results were observed in chicken hearts as depicted in FIG. 1B. After the decellularizing procedures, the acellular hearts appeared to be semi-transparent as compared with the naïve hearts (i.e., the hearts without any of the treatment described in Example 1.1 except washed with copious amounts of water) (FIGS. 1A and 1B).

Figure 2A:
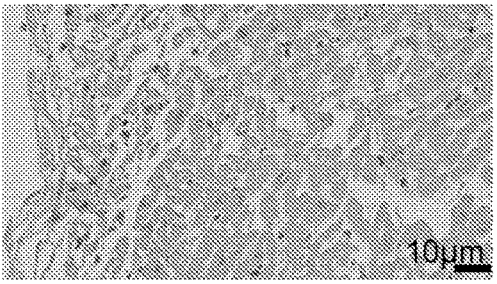
FIGS. 2A to 2D are photographs of hematoxylin and eosin staining (H&E staining) according to Example 1.2 of the present disclosure.
Figure 2A:
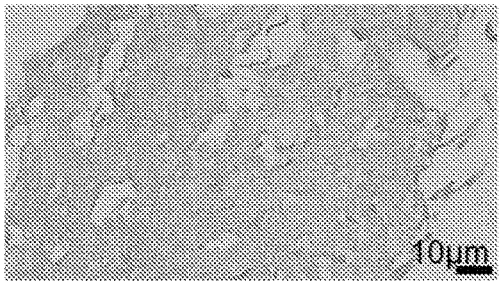
Figure 2A:
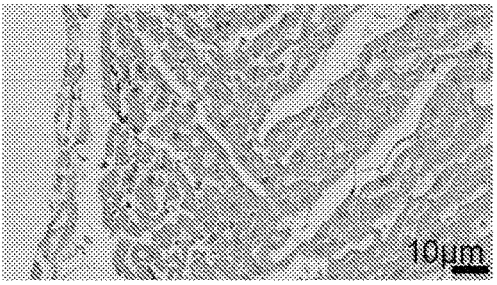
Figure 2A:
Figure 2A:
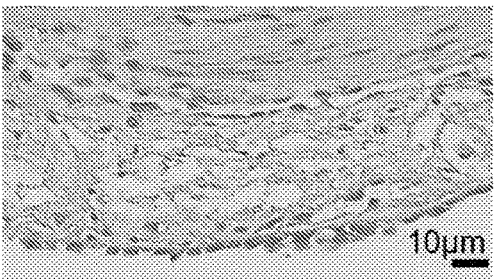
Figure 2A:
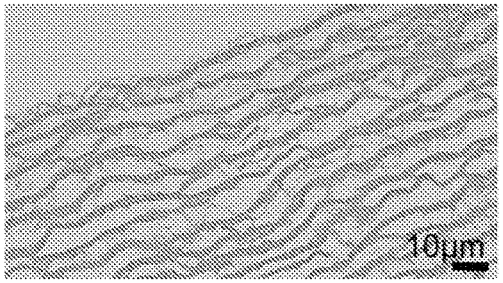
Figure 2B:
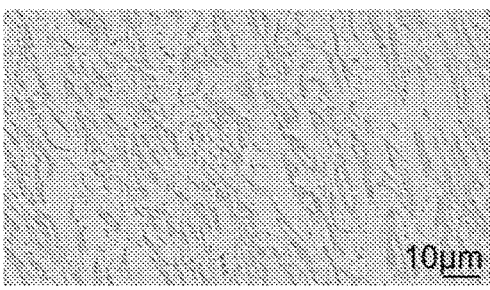
Figure 2B:
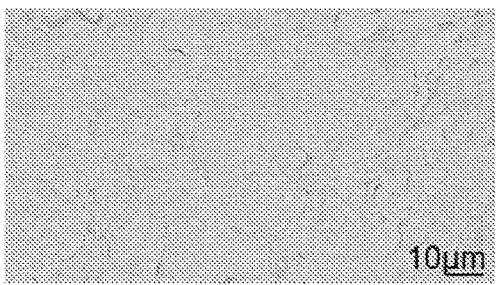
Figure 2B:
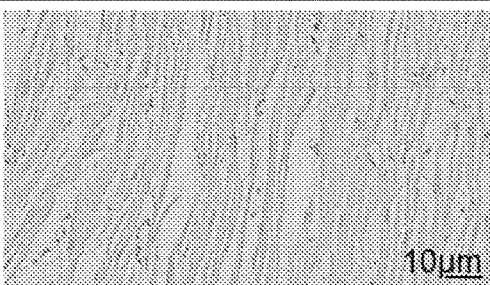
Figure 2B:
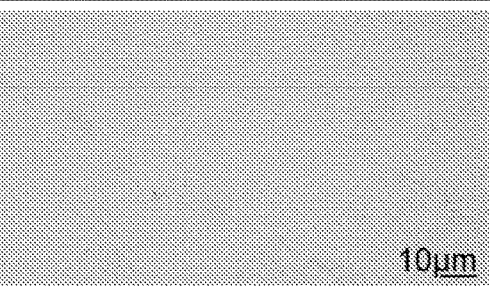
Figure 2B:
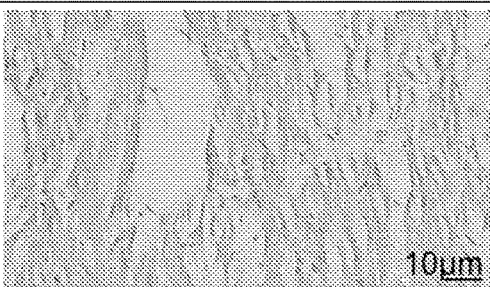
Figure 2B:
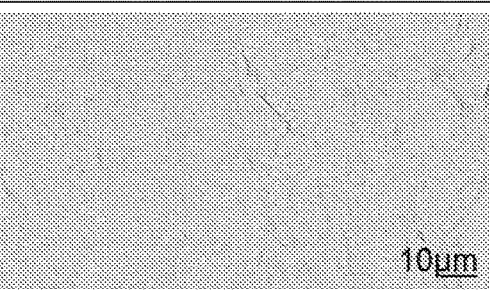
Figure 2C:
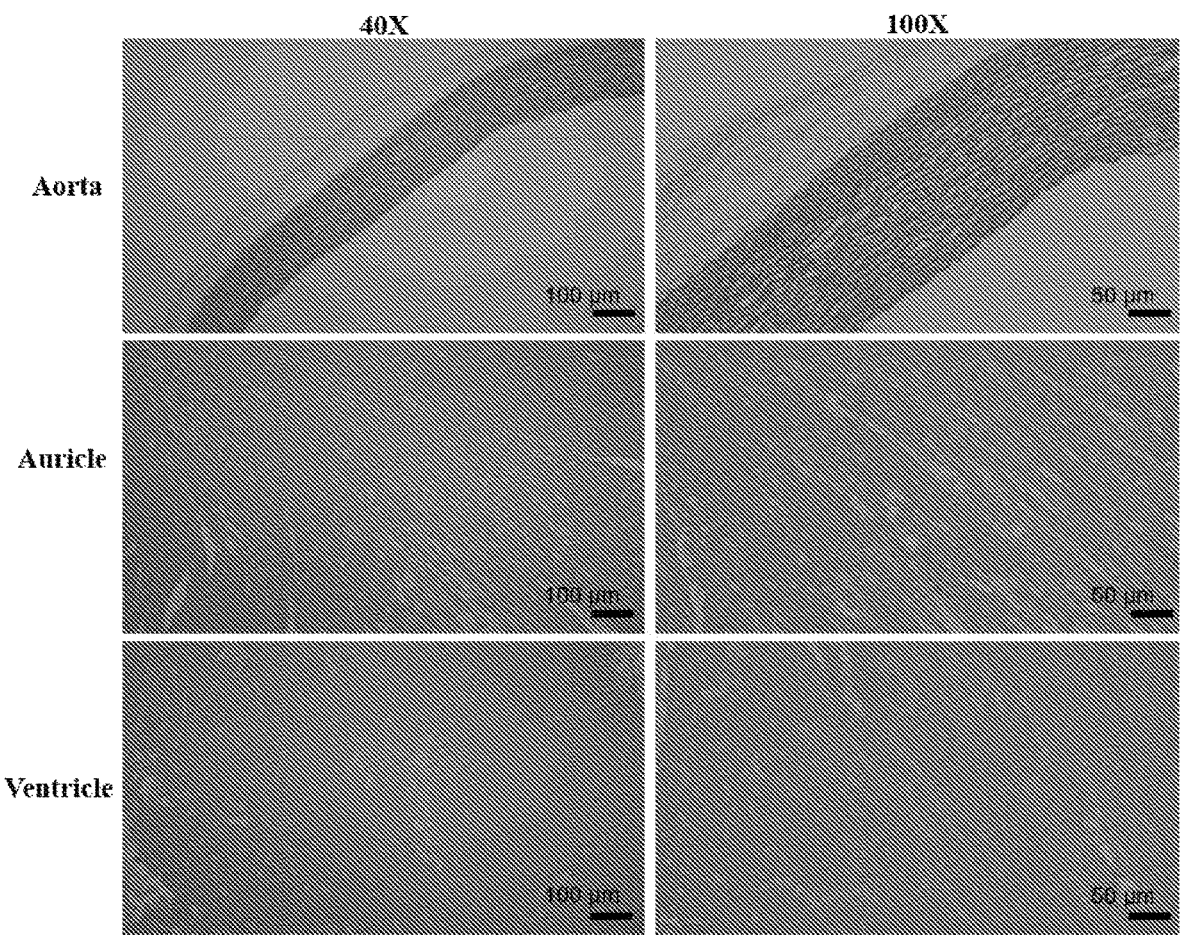
Figure 2D:
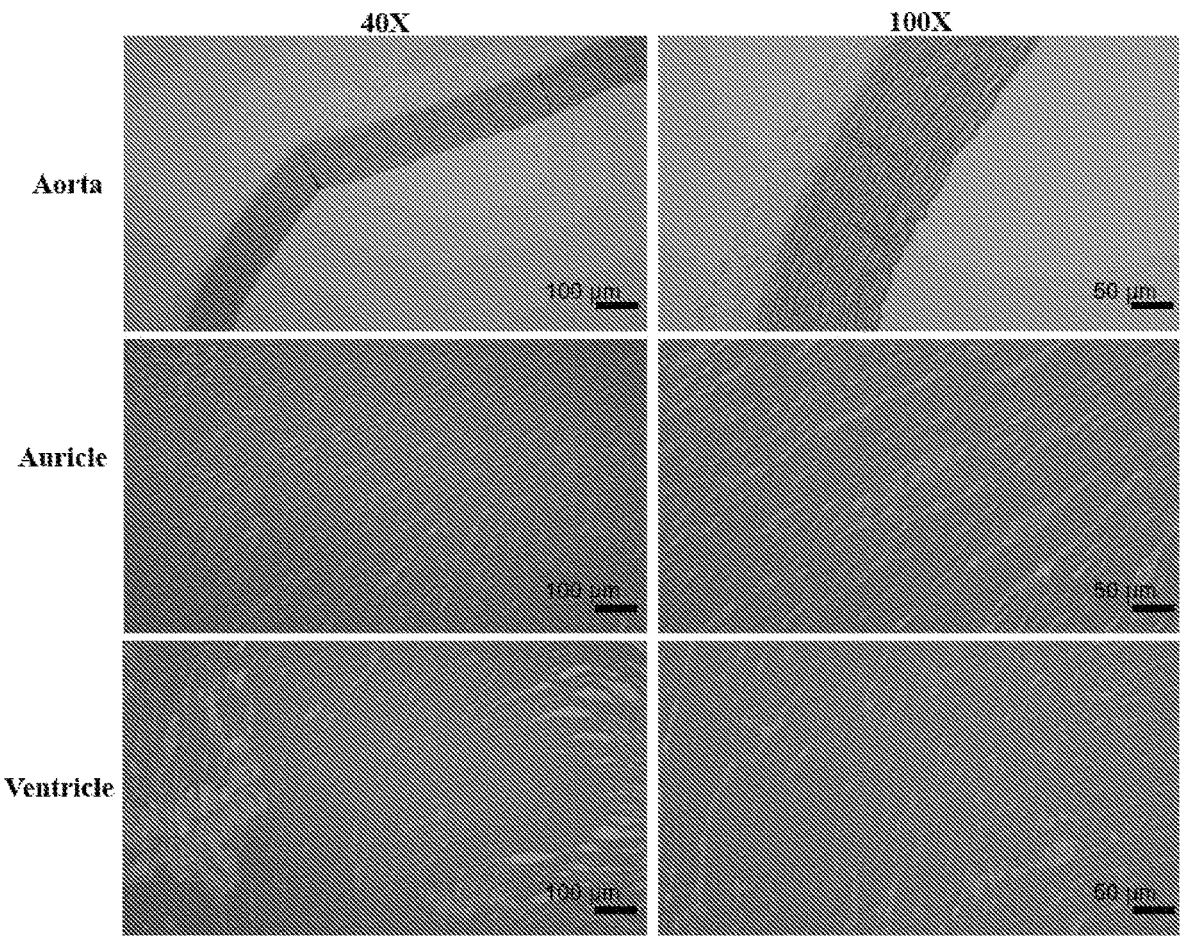
Figure 3A:
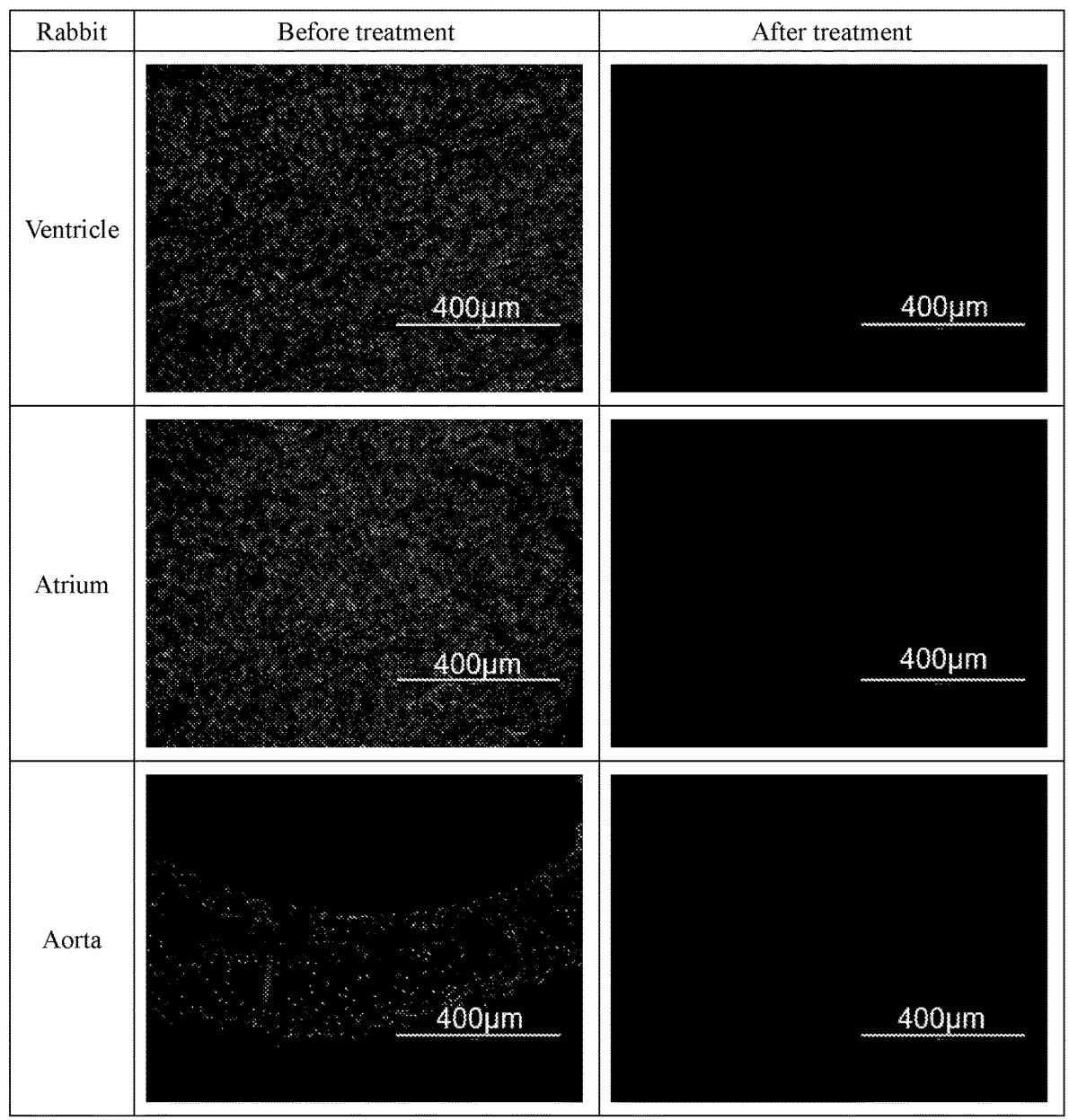
FIGS. 3A to 3C are photographs of 4',6-diamidino-2-phenylindole (DAPI) staining according to Example 1.2 of the present disclosure.
Figure 3B:
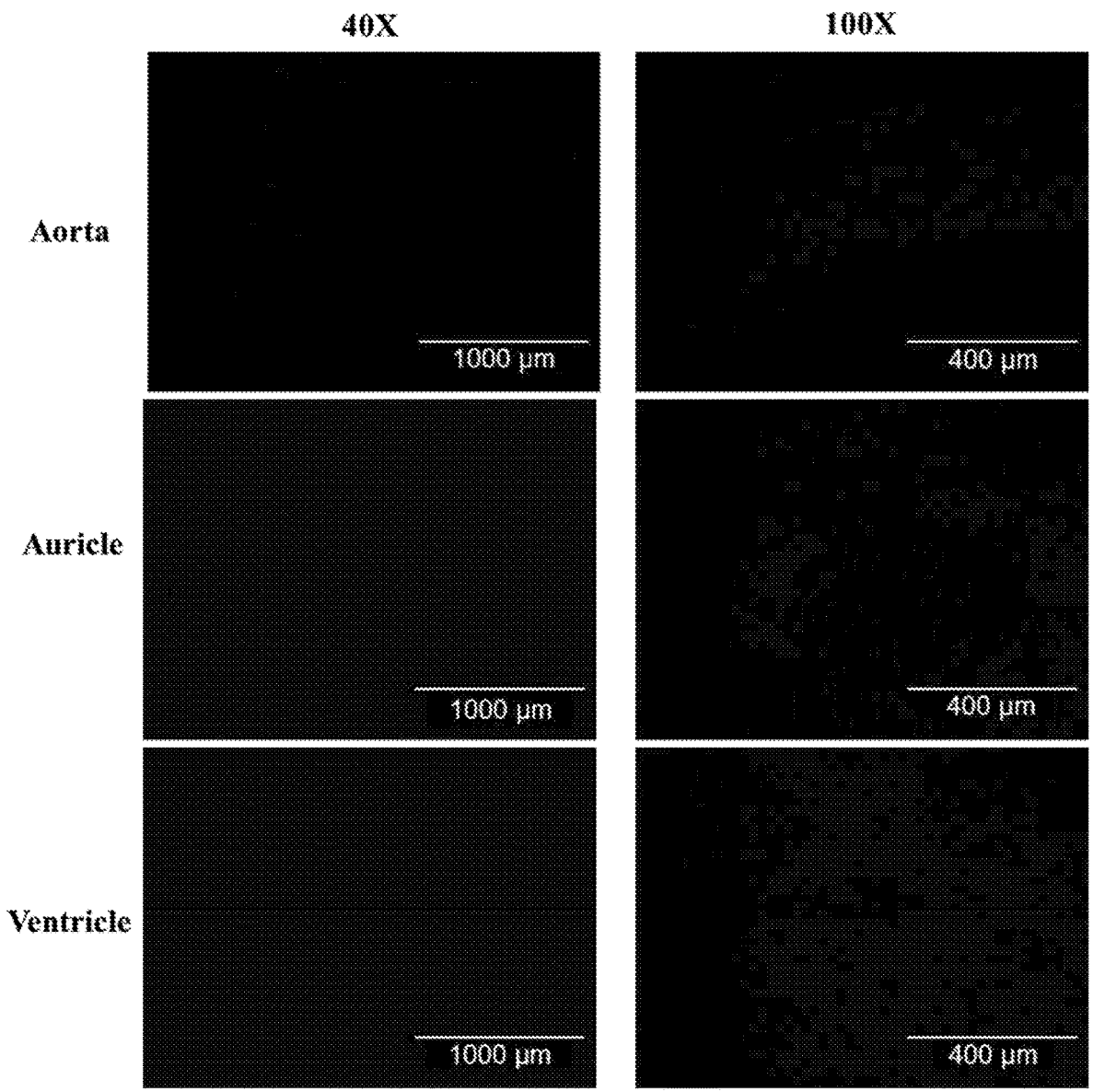
Figure 3C:
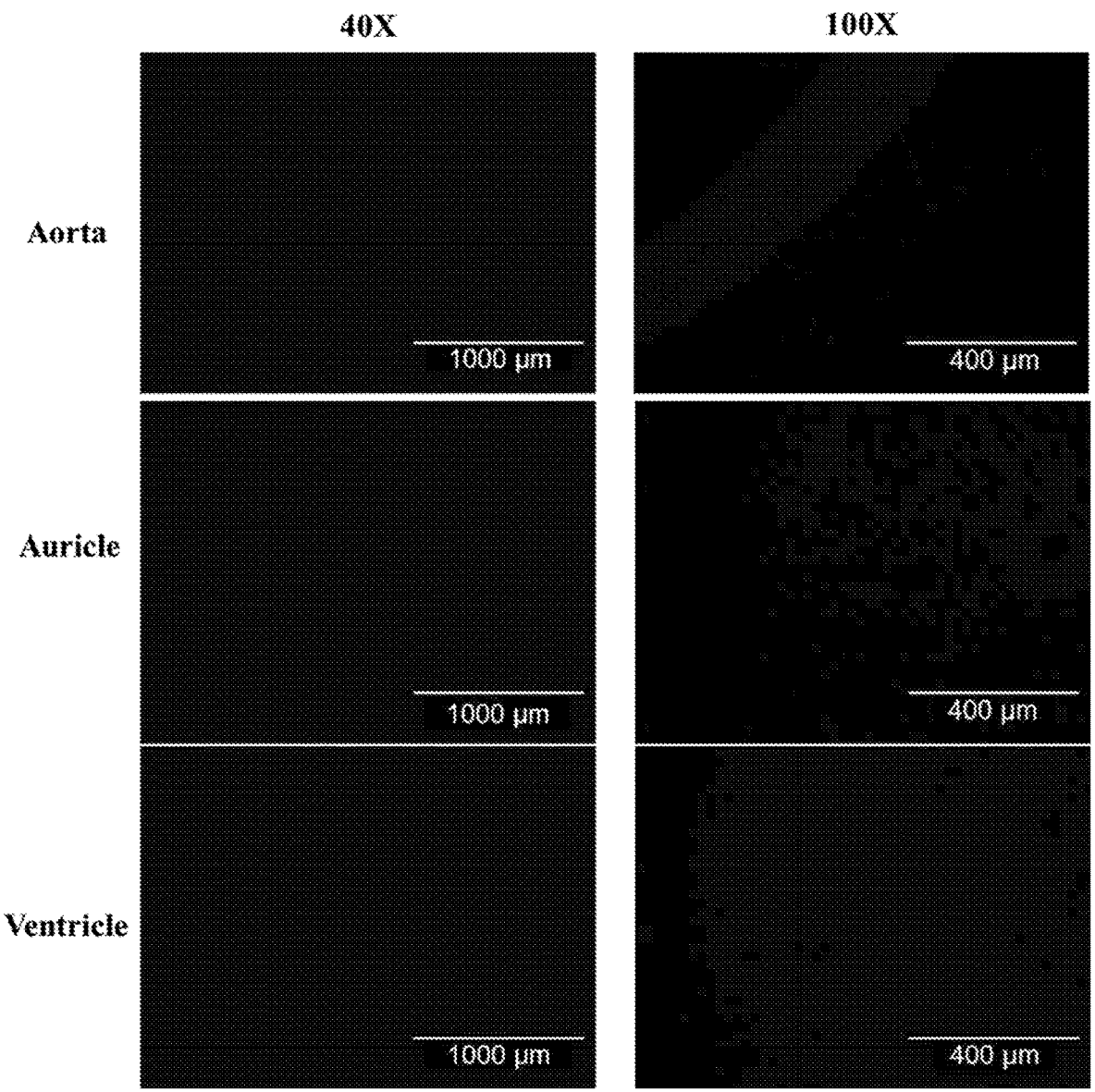
Figure 4:
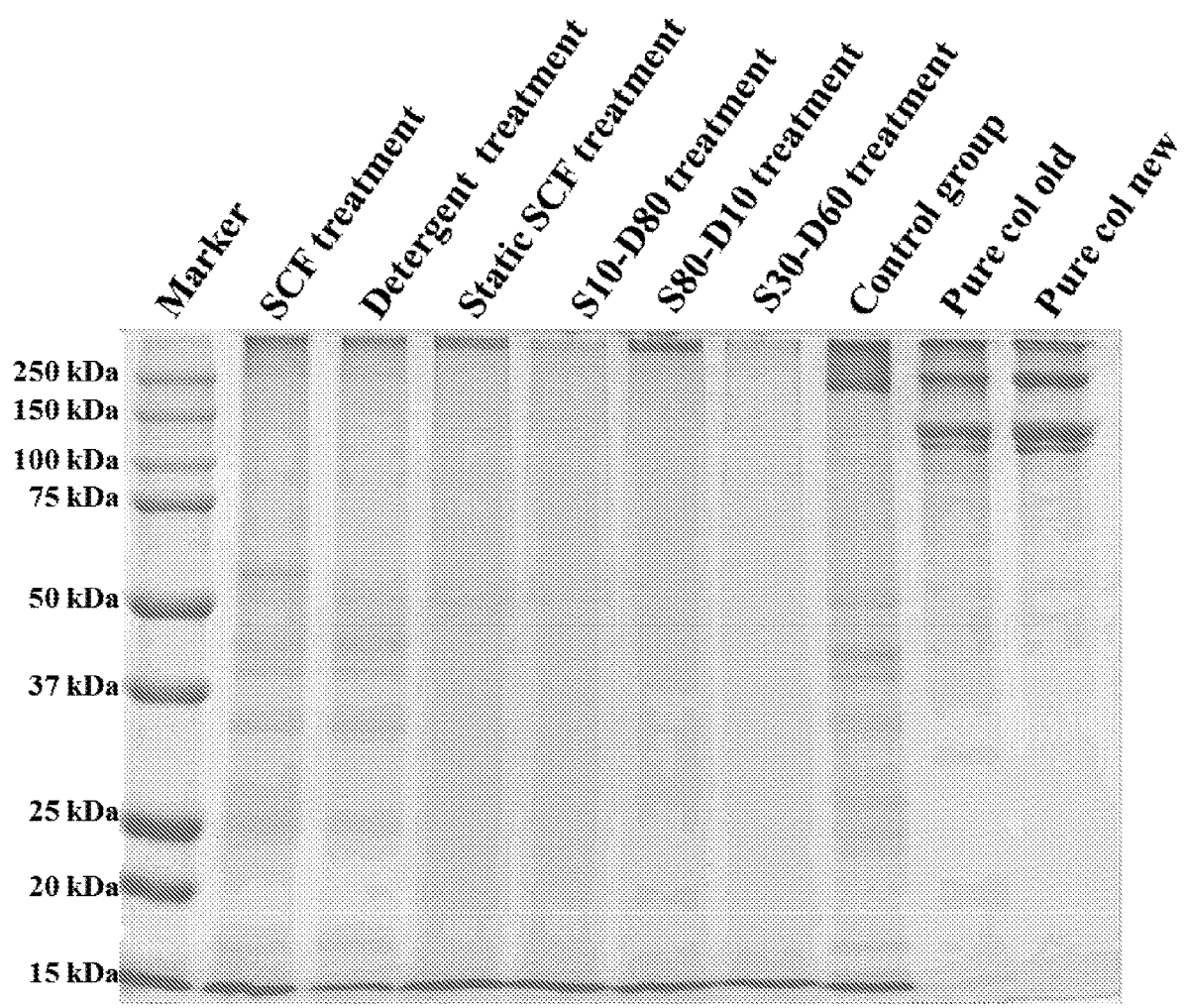
FIG. 4 is the data of western blot according to Examples of the present disclosure. SCF treatment: the protein sample of the decellularized heart produced by the SCF treatment of Comparative Example A. Detergent treatment: the protein sample of the decellularized heart produced by the detergent treatment of Comparative Example B. Static SCF treatment: the protein sample of the decellularized heart produced by the static SCF treatment of Comparative Example C. S10-80 treatment, S80-D10 treatment, S30-D60 treatment: the protein samples of decellularized hearts respectively produced by the decellularizing procedures as specified in Example 1.1. Control group: untreated hearts that are not subjected to any decellularizing treatment except washed with copious amounts of water. Pure col old: standard type I collagen; Pure col new: standard type I collagen.

The conformation of the acellular hearts was further examined by H&E staining, and DAPI staining. The data of H&E staining demonstrated that compared with the control group (i.e., untreated hearts), the present S30-D60 decellularizing procedure substantially removed all resident cells form the heart, and thus, no cell was detected in the S30-D60 acellular heart (FIGS. 2A and 2B). Similarly, after the S10-D80 or S80-D10 decellularizing procedure, no cell signal was detected by H&E staining in the S10-D80 and S80-D10 acellular hearts (FIGS. 2C and 2D). The data of DAPI staining further confirmed that untreated hearts had a relatively high level of DNA counts, while the present method effectively removed cellular matters in the S30-D60 acellular heart (FIG. 3A). The decellularizing effect was also observed in the S10-D80 and S80-D10 acellular hearts, where no DNA signal were detected under fluorescence microscope (FIGS. 3B and 3C). According to the quantified results, the present decellularizing procedures, including the S30-D60, S10-D80, and S80-D10 decellularizing procedure, removed more than 90% of cellular matters (FIG. 4).

Figure 5:
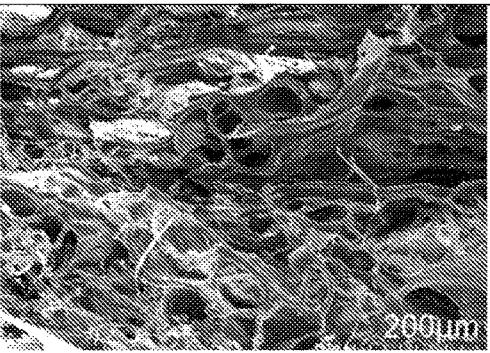
FIG. 5 are photographs of scanning electron microscope (SEM) at the magnitude of 400× that depict the fibril structure of hearts before and after decellularizing treatment according to Example 1.2 of the present disclosure.
Figure 5:
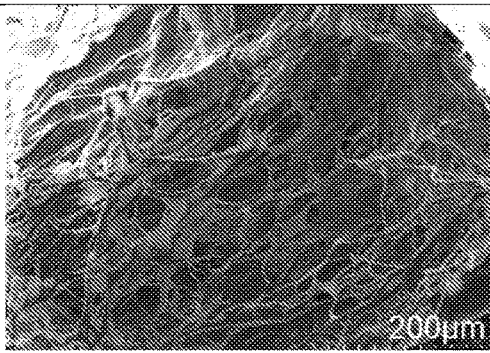
Figure 5:
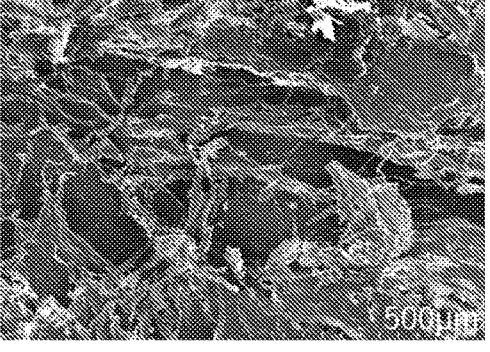
Figure 5:
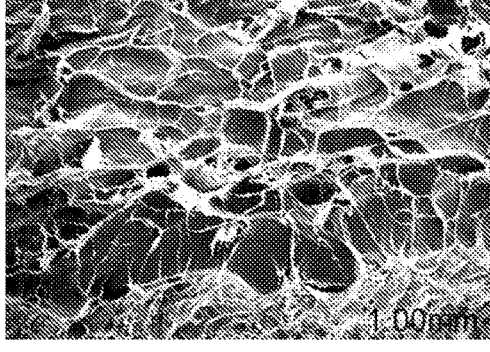
Figure 6:
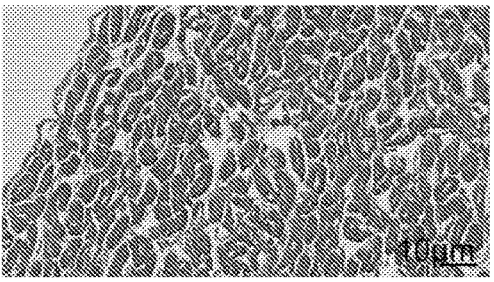
FIG. 6 are photographs of Masson's Trichrome Staining at the magnitude of 400× that depict the level and distribution of collagen of hearts before and after decellularizing treatment according to Example 1.2 of the present disclosure.

In addition to the decellularizing effect, whether the present methods would destroy the scaffold structure of hearts was also evaluated. As the SEM images depicted in FIG. 5, in comparison with the control group, the S30-D60 acellular heart possessed relatively intact fibril structure that may serve as a biological scaffold for cells to grow thereon after transplantation. The data of Masson's Trichrome staining depicted in FIG. 6 further confirmed that the level and distribution of collagen in the S30-D60 acellular heart were similar with that of the control group.

Taken together, these results demonstrated that the present decellularizing procedures, including the S30-D60, S10-D80, and S80-D10 decellularizing procedures, were useful in removing cellular matters from the target organ (e.g., heart) without destroying the fibril structure of the target organ.

Comparative Example Acellular Heart Produced by Comparative Methods

In addition to the methods exemplified in Example 1, the present invention also treated the naïve hearts with alternative decellularizing methods so as to evaluate their decellularizing effect.

A. Preparation and Characterization of Decellularized Hearts by SCF Treatment

The hearts harvested from rabbits were subjected to the SCF treatment operated at a pressure of 100 bar, at 35° C. for 3 hours, in which 16 ml ethanol (75%) was present in the vessel. The SCF treated hearts were then examined by microscope, and H&E and DAPI staining.

Figure 7A:
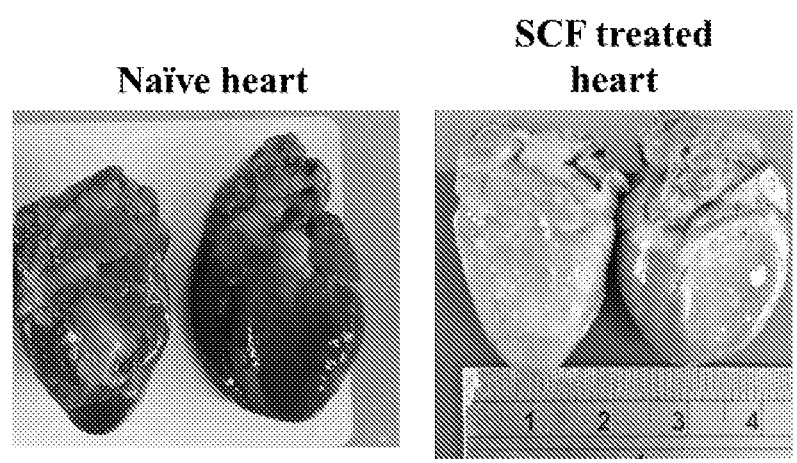
FIG. 7A to 7C are photographs that depict the decellularizing hearts produced by the SCF treatment of Comparative Example A.
Figure 7B:
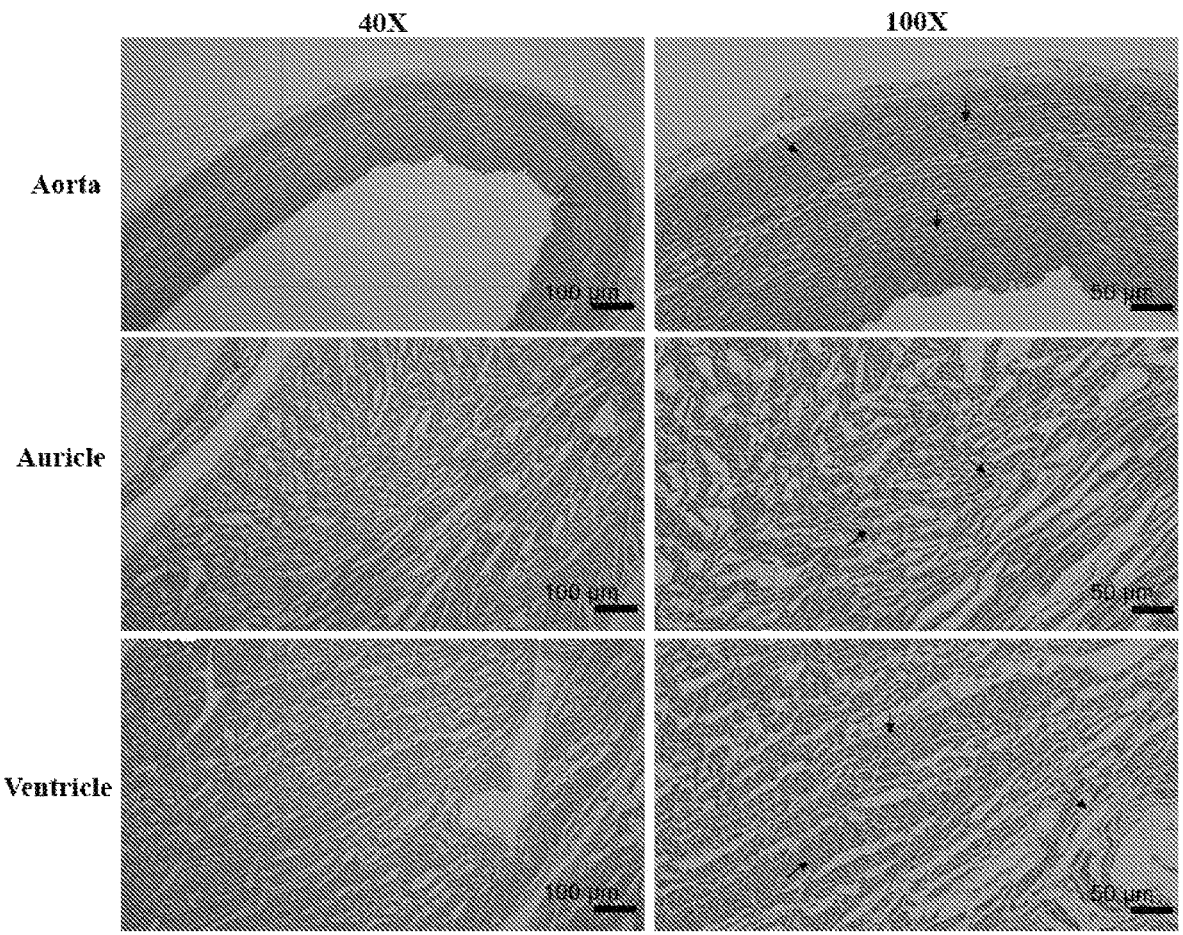
Figure 7C:
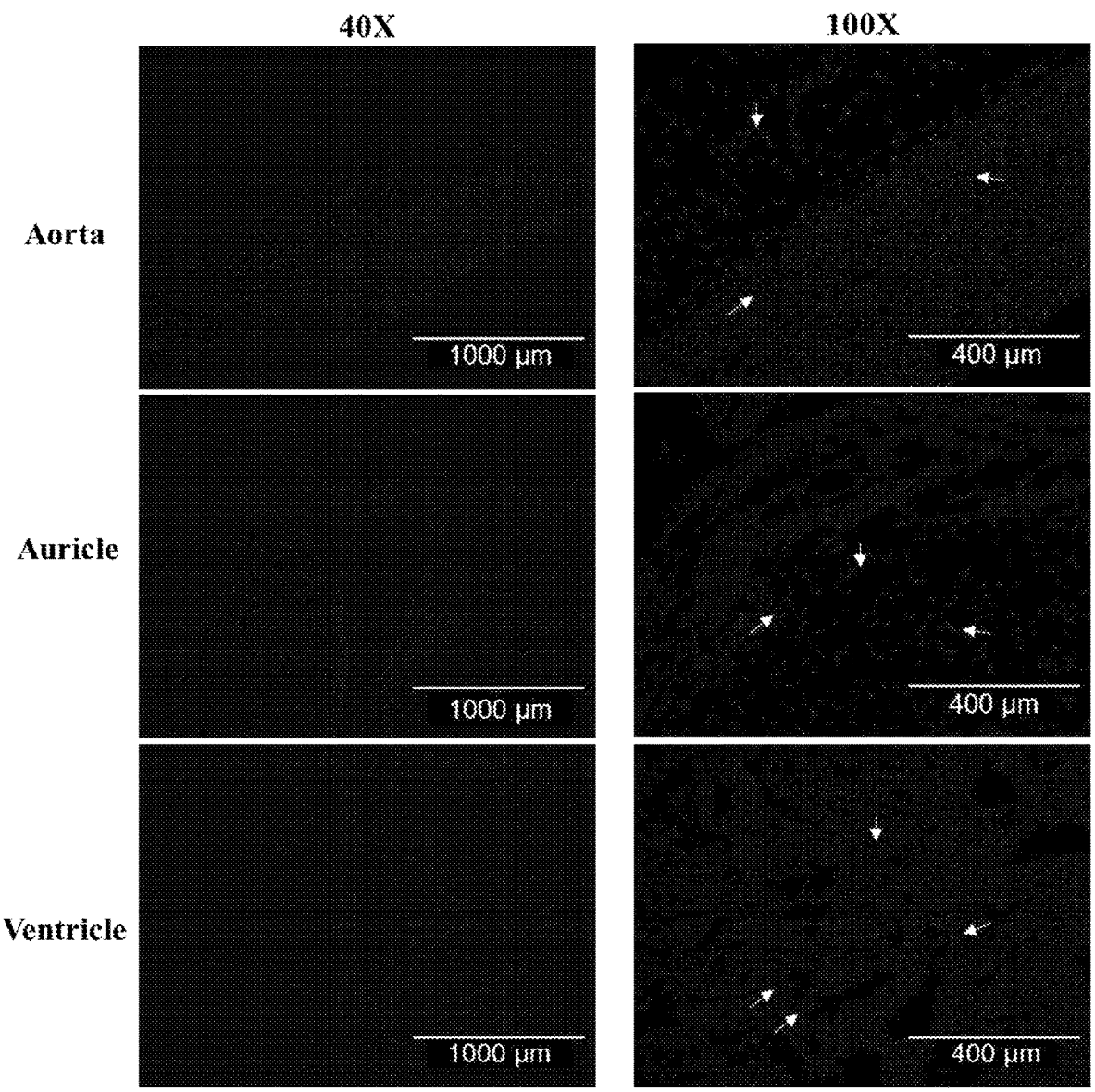

As the photographs depicted in FIG. 7A, the SCF treatment did not obviously alter the morphology of hearts. However, such the SCF treatment exhibited a poor decellularizing effect on hearts, in which about 80% of resident cells remained in the aorta, auricle and ventricle of the hearts (FIG. 7B; the resident cells were indicated by arrows). The data of DAPI staining also indicated that high level of DNA counts was detected in the SCF treated hearts (FIG. 7C; the resident DNA molecules were indicated by arrows).

B. Preparation and Characterization of Decellularized Hearts by Detergent Treatment The hearts harvested from rabbits were subjected to a magnetic stir plate and magnetic stirrer, and being rotated in distilled water at 4° C., 95 rpm for 24 hours. After replacing the distilled water with a 0.05% ammonium hydroxide solution containing 0.5% TRITON™ X-100, the hearts were rotated at 4° C., 95 rpm for 72 hours. Then, the hearts were washed by distilled water at 4° C., 95 rpm for 24 hours thereby removing residual detergent.

Figure 8A:
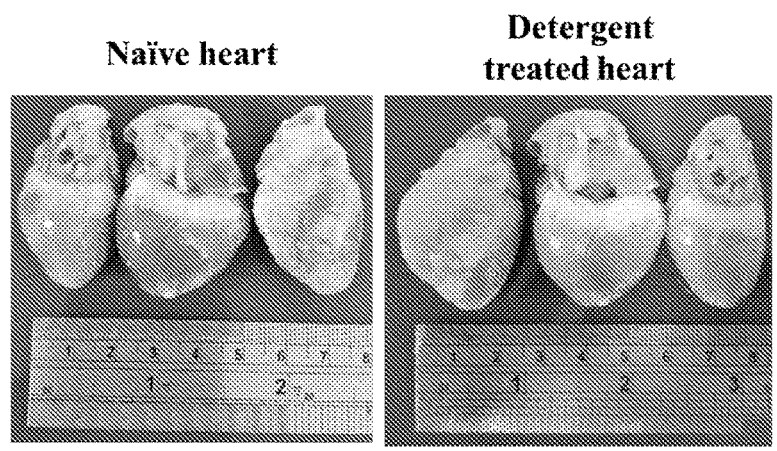
FIG. 8A to 8C are photographs that depict the decellularizing hearts produced by the detergent treatment of Comparative Example B.
Figure 8B:
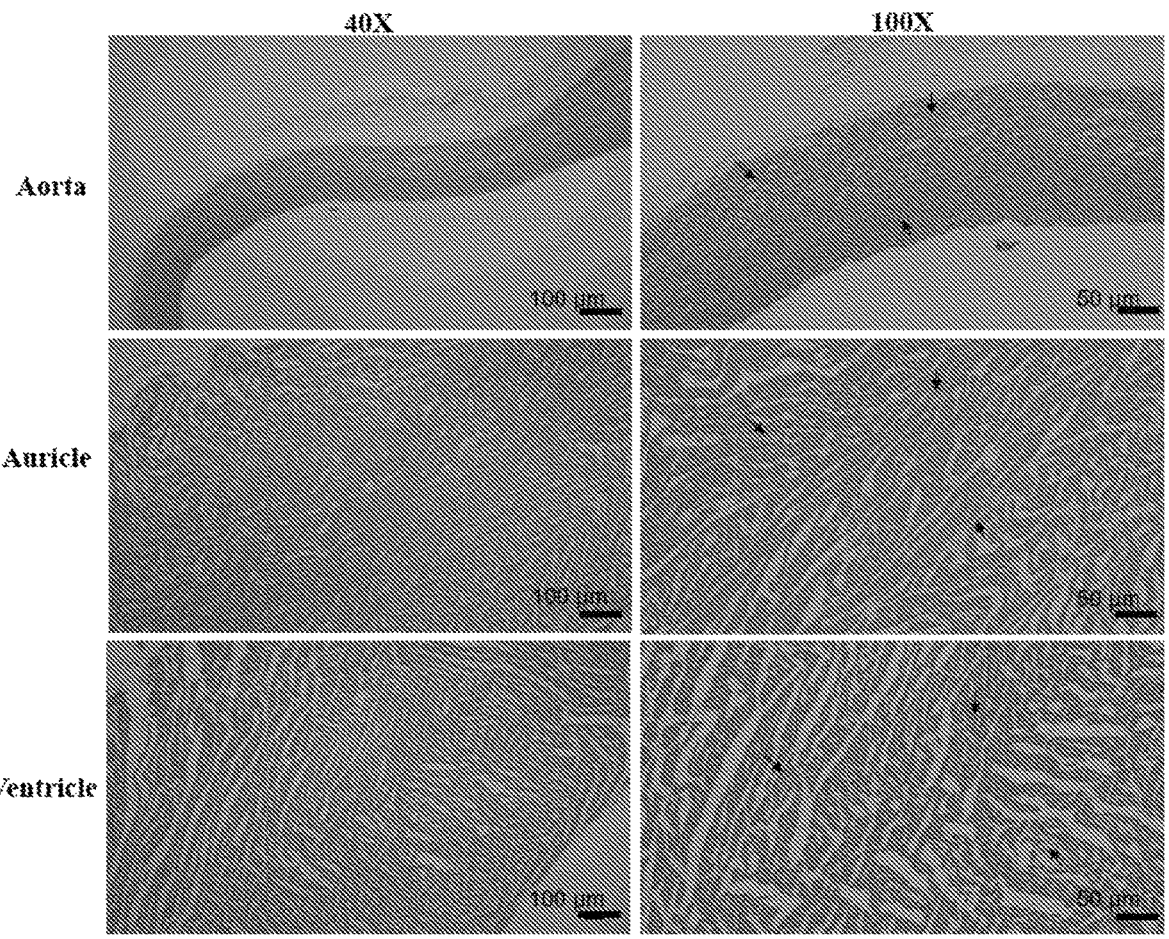
Figure 8C:
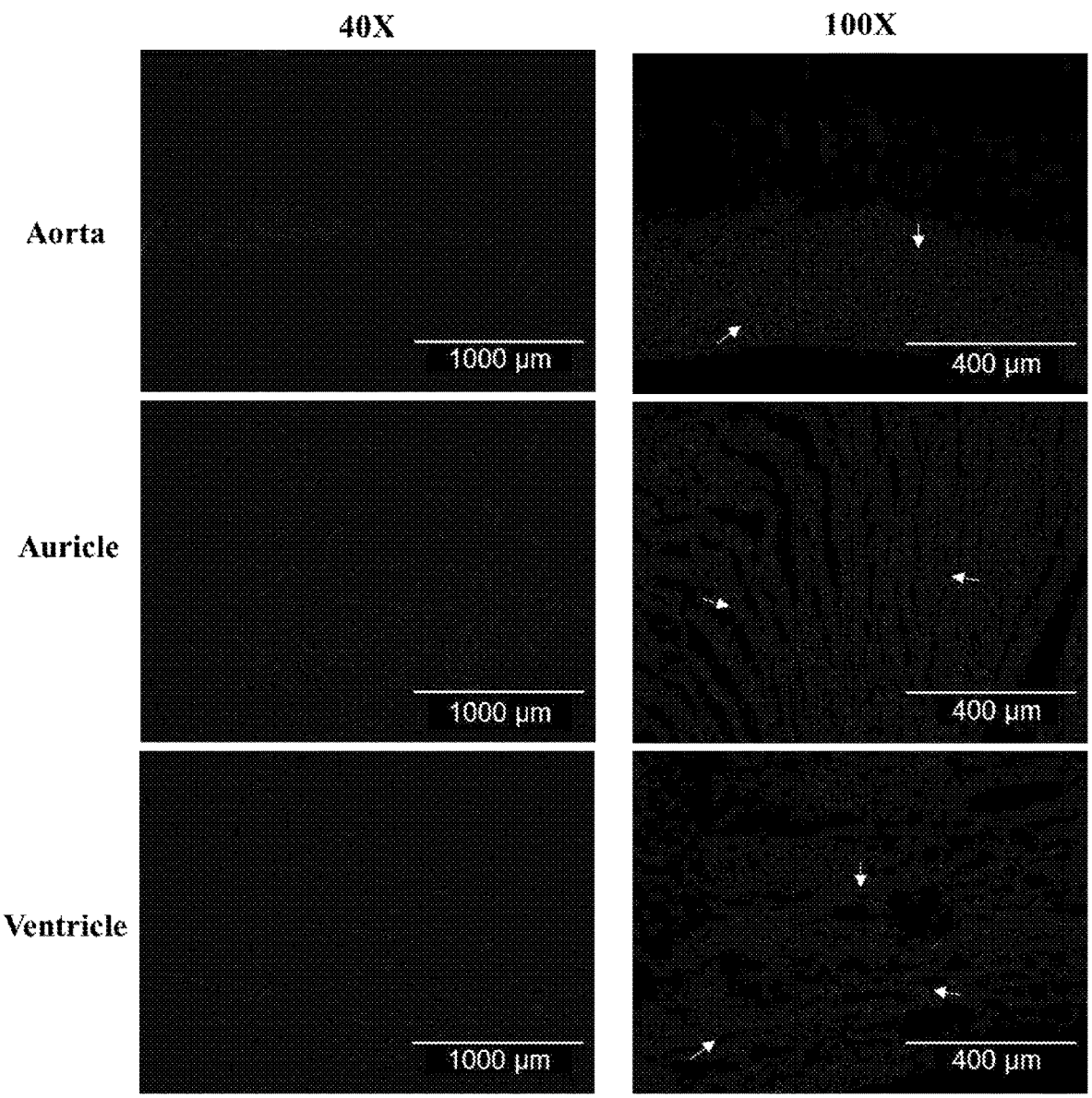

The photographs of FIG. 8A indicated that the detergent treatment did not obviously affect the structure of hearts. Nonetheless, about 70% of cellular matters (i.e., the resident cells and DNA molecules) remained in the detergent treated hearts (FIGS. 8B and 8C; the cellular matters were indicated by arrows), demonstrating such the detergent treatment may not provide a satisfactory effect on producing acellular organs.

C. Preparation and Characterization of Decellularized Hearts by Static SCF Treatment The decellularizing procedure of this example was similar to that of Example 1.1, except the SCF treatment step, in which the rabbit hearts were merely treated with static SCF treatment without any dynamic SCF treatment. Specifically, the hypertonic/hypotonic treated hearts were subjected to the static $ScCO_2$ treatment at a pressure of 100 bar, at 35° C. for 3 hours in the present of 16 ml ethanol (75%) in the vessel, followed by the neutralization step as described in Example 1.1.

Figure 9A:
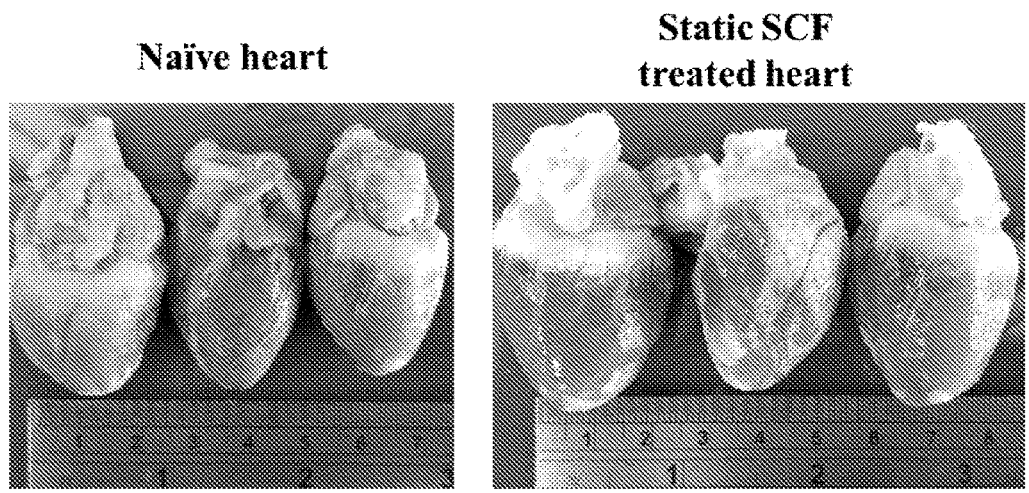
FIG. 9A to 9C are photographs that depict the decellularizing hearts produced by the static SCF treatment of Comparative Example C.
Figure 9B:
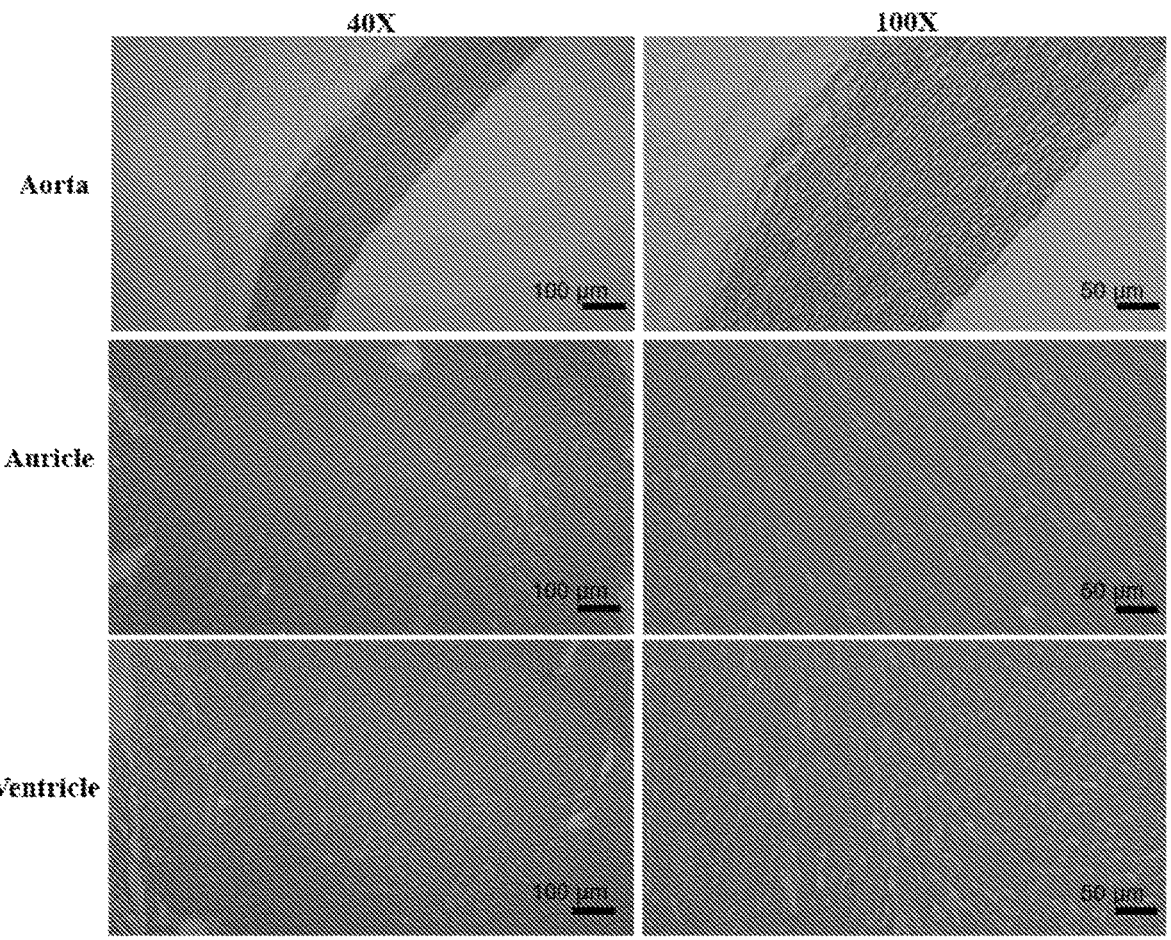
Figure 9C:
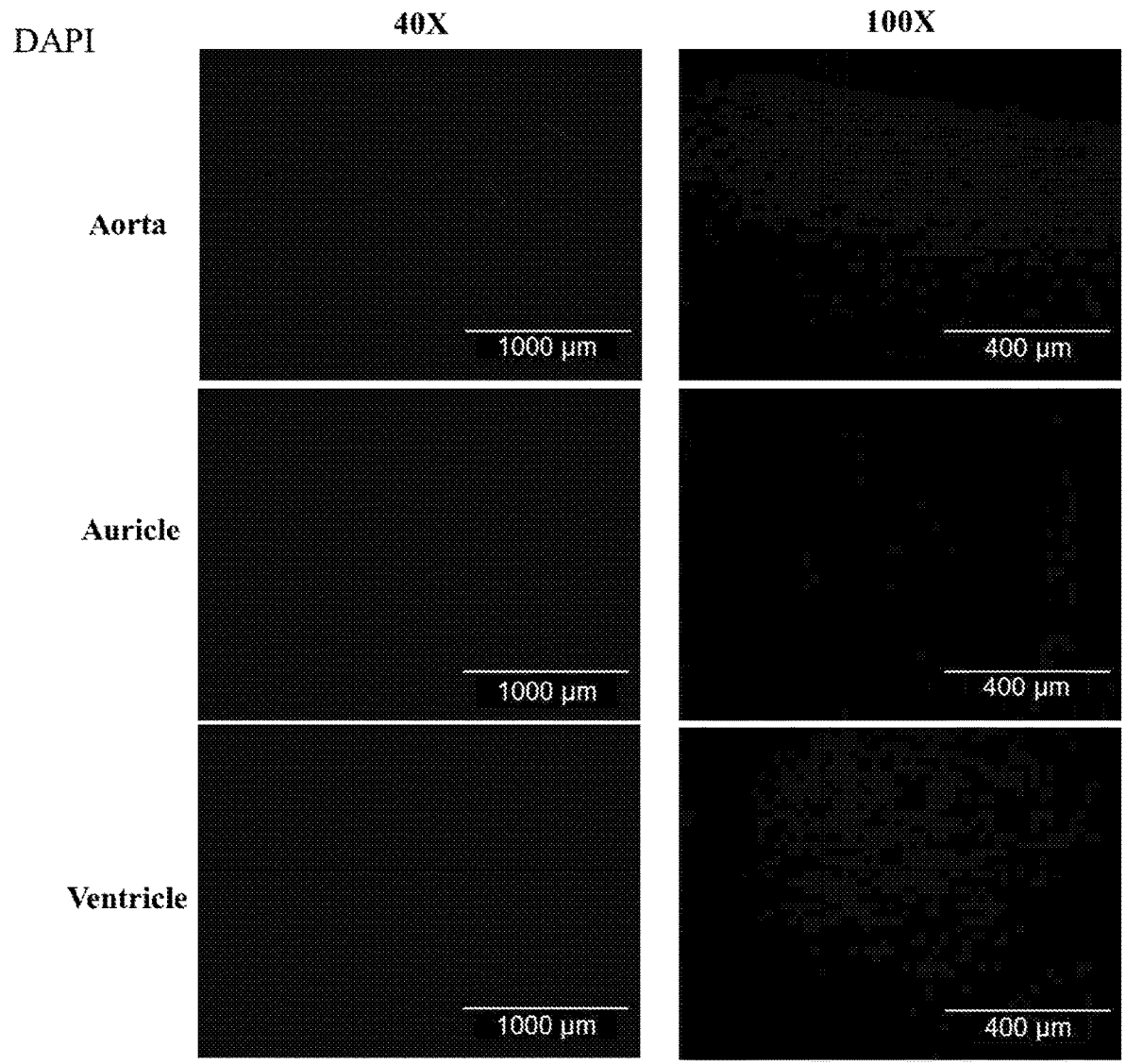

The data of FIGS. 9A-9C indicated that the static SCF treatment was effective in removing cellular matters (including resident cells and DNA molecules as respectively depicted in FIGS. 9B and 9C) from hearts; however, such decellularizing treatment harmfully destroyed the structure of the organ, in which compared with the control group, the hearts treated with the static SCF treatment exhibited a swollen morphology (FIG. 9A).

As the data depicted in FIG. 4, compared with the acellular hearts produced by the present methods (i.e., the methods of Example 1), where substantially no cellular matter was detected, there existed a relatively high level of cellular matters in the hearts treated by comparative methods. The data demonstrated that the present methods exhibited a superior decellularizing effect over other methods (including the SCF, detergent, and static SCF treatments).

In conclusion, the present disclosure provides a method of efficiently removing cellular matters from a target organ (e.g., a heart) without destroying its native structure and conformation. Compared with the decellularized organ produced by other methods as exemplified in Comparative Examples A-C of the present disclosure that either had high level of cellular matters remained therein, or exhibited a destructive structure, the acellular organ produced by the present method provides a more potential and safer means to treat various diseases, e.g., heart diseases.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A method of producing an acellular organ, comprising:
   (a) subjecting an organ to a first supercritical fluid (SCF) in the presence of a first co-solvent under a first pressure of 200-500 bar at a first temperature between 30-50° C. for a first period of 10-100 minutes; and
   (b) subjecting the first SCF treated organ of the step (a) with a continuous flow of a second SCF in the presence of a second co-solvent under a second pressure of 200-500 bar at a second temperature between 30-50° C. for a second period of 10-100 minutes, wherein the flow rate of the second SCF is 10-30 liter per minute;
   wherein, the method does not comprise the step of treating the organ with an agent selected from the group consisting of an enzyme, an ion chelating agent, a detergent, a glycerol, and a combination thereof.

2. The method of claim 1, wherein the first and second SCFs are independently selected from the group consisting of supercritical carbon dioxide ($ScCO_2$), supercritical nitrous oxide ($ScN_2O$), supercritical alkane, supercritical alkene, supercritical alcohol, supercritical acetone, and a combination thereof.

3. The method of claim 2, wherein each of the first and second SCFs is the $ScCO_2$.

4. The method of claim 3, wherein
   each of the first and second pressures is 350 bar;
   each of the first and second temperatures is 40° C.;
   each of the first and second periods is 10-80 minutes; and
   the flow rate of the second SCF is 20 liter per minute.

5. The method of claim 4, wherein the first period is 30 minutes, and the second period is 60 minutes.

6. The method of claim 4, wherein the first period is 10 minutes, and the second period is 80 minutes.

7. The method of claim 4, wherein the first period is 80 minutes, and the second period is 10 minutes.

8. The method of claim 1, wherein each of the first and second co-solvents is 30-100% (vol %) ethanol.

9. The method of claim 8, wherein each of the first and second co-solvents is 75% (vol %) ethanol.

10. The method of claim 1, further comprising, prior to the step (a),
    (1) immersing the organ in a hypertonic solution for 10-60 minutes; and
    (2) immersing the hypertonic solution treated organ of the step (1) in a hypotonic solution for 10-60 minutes.

11. The method of claim 10, wherein the hypertonic solution is a salt solution containing 0.5-4.0 M NaCl, and the hypotonic solution is water.

12. The method of claim 11, wherein
    in the step (1), the organ is immersed in the salt solution containing 2.0 M NaCl for 30 minutes; and
    in the step (2), the salt solution treated organ is immersed in water for 30 minutes.

13. The method of claim 10, wherein the steps (1) and (2) are repeated for at least two times.

14. The method of claim 1, further comprising, after the step (b), subjecting the second SCF treated organ to a solution containing 0.01-1.0 N NaOH.

15. The method of claim 14, wherein the solution contains 0.1 N NaOH.

16. The method of claim 1, wherein the organ is heart, intestine, lung, spleen, kidney, liver, stomach, pancreas, bladder, colon, rectum, or brain.

17. The method of claim 16, wherein the organ is heart.

18. The method of claim 1, wherein the organ is derived from a subject selected from the group consisting of, pig, cow, sheep, goat, rabbit, monkey, chicken, and human.

* * * * *